United States Patent [19]

Boyle et al.

[11] Patent Number: 4,945,157
[45] Date of Patent: Jul. 31, 1990

[54] NOVEL EXTRACTION PROCEDURE FOR PROTEIN G

[75] Inventors: Michael D. P. Boyle; Ervin Faulmann, both of Gainesville, Fla.

[73] Assignee: University of Florida, Gainesville, Fla.

[21] Appl. No.: 199,548

[22] Filed: May 27, 1988

[51] Int. Cl.$^5$ .......................... C07K 3/28; C07K 15/04
[52] U.S. Cl. .................................... 530/409; 530/415; 530/416; 530/417; 530/825
[58] Field of Search ............... 530/409, 415, 416, 417, 530/825

[56] References Cited

U.S. PATENT DOCUMENTS

| | | | |
|---|---|---|---|
| 3,850,798 | 11/1974 | Sjoquist | 530/825 X |
| 3,995,018 | 11/1976 | Sjöquist | 530/825 X |
| 4,448,768 | 5/1984 | Colman et al. | 530/825 X |
| 4,594,244 | 6/1986 | Lehner et al. | 530/825 X |
| 4,644,057 | 2/1987 | Bicker et al. | 530/409 |
| 4,757,134 | 7/1988 | Blake et al. | 530/350 |
| 4,812,441 | 3/1989 | Kawai et al. | 530/825 X |

FOREIGN PATENT DOCUMENTS 0131142  1/1985  European Pat. Off. .

OTHER PUBLICATIONS

Myhre, E. B. and Kronvall, G. (1981) "Immunoglobulin Specificities of Defined Types of Streptococcal Ig Receptors," In *Basic Concepts of Streptococci and Streptococcal Diseases* (Holm, S. E. and Christensen, P., eds.) pp. 209–210, Reed Book, Ltd., Chertsey, Surrey.

Boyle, M. D. P. (1984) "Applications of Bacterial Fc Receptors in Immunotechnology," BioTechniques 2:334–340.

Reis, K. J., Ayoub, E. M., and Boyle, M. D. P. (1985) "A Rapid Method for the Isolation and Characterization of a Homogeneous Population of Streptococcal Fc Receptors," J. Microbiol. Methods 4:45–58.

Bjorck, L. and Kronvall, G. (1984) "Purification and Some Properties of Streptococcal Protein G, a Novel IgG-Binding Reagent," J. Immunol. 133: 969–974.

Boyle, M. D. P. and Reis, K. J. (1987) "Bacterial Fc Receptors," Biotechnology 5:697–703.

*Primary Examiner*—Howard E. Schain
*Attorney, Agent, or Firm*—Saliwanchik & Saliwanchik

[57] ABSTRACT

Protein G from wild-type group G or group C streptococci is obtained by an extracting process using cyanogen bromide. The process gives yields ranging up to 60-fold better than the best prior art process known.

9 Claims, 4 Drawing Sheets

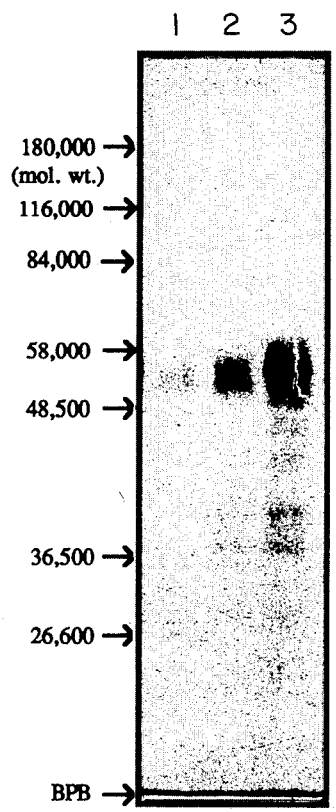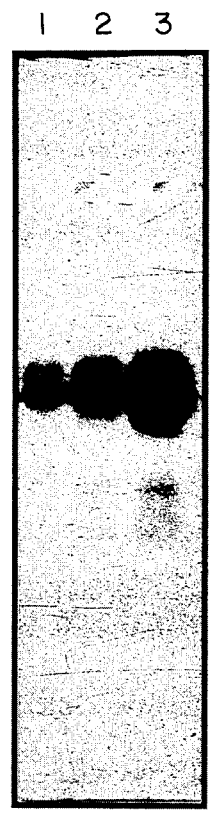

180,000 → (mol. wt.)
116,000 →
84,000 →

58,000 →
48,500 →

36,500 →

26,600 →

BPB →

NOVEL EXTRACTION PROCEDURE FOR PROTEIN G

Work disclosed herein was supported, in part, by a grant from the National Science Foundation, i.e., NSF, 8500512 DCB, and by Gator Microbiologicals Incorporated.

BACKGROUND OF THE INVENTION

Bacterial Fc receptors have been identified by their ability to bind to a site within the constant region of various classes and subclasses of mammalian IgG (Myhre, E.B. and G. Kronvall. 1981. Immunoglobulin specificities of defined types of streptococcal Ig receptors. In: Basic Concepts of Streptococci and Streptococcal Diseases [Holm, S.E. and P. Christensen, eds.]pp. 209–210, Reed Book, Ltd., Chertsey, Surrey) The Fc region of the IgG antibody molecule is associated with the biological effector properties of the molecule while the antigenic recognition elements are located in the two identical Fab portions of the antibody. Consequently, the interaction of bacterial Fc receptors with constant region determinants on the heavy chain of IgG does not interfere with the ability of the antibody to recognize its antigen; it is this property that makes these receptors so useful as tracers of antibody-antigen interaction (See Boyle, M.D.P. (1984) "Applications of bacterial Fc receptors in immunotechnology," Biotechniques 2:334–340.)

To date, six types of bacterial receptors have been described based on the reactivity of whole bacteria with different classes and subclasses of mammalian immunoglobulins. The most extensively characterized receptor is the type I receptor isolated from *Staphylococcus aureus*, and more commonly designated protein A. The type II receptor is found on a few group A streptococci. The type III receptor, also known as protein G, is present on many group C streptococci and on some human group G streptococci The type IV receptor is isolatable from a few bovine group G streptococci, the type V receptor is found on certain *Streptococcus zooepidemicus* strains, and the type VI receptor has been recently reported on selected strains of *S. zooepidemicus*

The efficient recovery and purification of bacterial receptors from wild-type bacteria, i.e., non-recombinant bacteria, are critical to the ultimate commercial use of these receptors. The best prior art process known for the recovery of protein G from group G or group C streptococci uses a proteolytic enzyme extraction procedure. See Reis, K. J., Ayoub, E. M., and Boyle, M. D. P. (1985) "A rapid method for the isolation and characterization of a homogenous population of streptococcal Fc receptors," J. Microbio. Methods 4:45-58; Bjorck, L. and Kronvall, G. (1984) "Purification and some properties of streptococcal protein G, a novel IgG-binding reagent," J. Immunol. 133:969-974; and European Patent Application No. 0 131 142, published on Jan. 16, 1985. The invention concerns the use of proteolytic enzymes, e.g., papain, trypsin and pepsin, to solubilize the protein G bound to the streptococcal cell wall. The EPO application also discloses U.S. Pat. No. 3,850,798 which uses trypsin to recover protein A.

Wild type protein G is distinguishable from the recombinant form of the protein by having the ability to bind not only to the Fc region of human IgG, but also to human albumin.

The prior art processes all use enzymatic hydrolysis as the method to extract either protein A or protein G. We have tried the trypsin extraction process to recover protein G from wild-type group G or group C streptococci and have been able to obtain a yield of ca. 10 mcg. of protein G from a gram of wet bacterial mass. Though this is an acceptable product yield, there is still a need to have a more efficient extraction process. Further, the proteolytic enzymes may degrade the protein G product. Thus, the prior art methods of extracting protein G from wild-type streptococcus may produce low molecular weight degraded forms of protein G, which are not as stable and cannot be radiolabeled without loss of functional activity (see Boyle, Michael D. P. and Reis, K. J. [1987]"Bacterial Fc receptors," Biotechnology 5:697–703).

BRIEF SUMMARY OF THE INVENTION

The subject invention concerns a novel improved process for recovering protein G from wild-type group G or group C streptococci. This improved process gives yields ranging up to 60-fold better than the best prior art process known. For example, yields of protein G of about 0.6 mg from a gram of wet weight bacterial mass have been obtained. The invention process, which is non-enzymatic, involves the use of cyanogen bromide to rapidly extract protein G from group G or group C streptococcus bacteria The reactive homoserine lactone on the carboxy terminus of the protein G can then be blocked by standard treatment with a source of primary amine, for example, Tris or glycine at high pH, ca. 8–10. Purified protein G can then be obtained by use of a number of standard techniques. For example, the protein can be purified by conventional molecular sieving chromatography, or ion exchange chromatography.

BRIEF DESCRIPTION OF THE DRAWINGS

FIG. 3 —Stained SDS-PAGE and western blot pattern of extracted proteins recovered from the active peak of the FPLC column. See FIG. 2. In 3A the concentrations of extract are 1 μg (lane 1), 3 μg (lane 2), and 10 μg (lane 3), respectively, stained with Coomassie stain. 3B is the western blot probed with $^{125}$I-human IgG Fc fragments.

DETAILED DESCRIPTION OF THE INVENTION

Upon treating a protein G positive group G or group C streptococcus preparation with cyanogen bromide for a sufficient time to solubilize substantially all the protein G, there is obtained an extract (soluble phase) rich in protein G. The reactive homoserine lactam on the carboxy terminus of the protein G can then be blocked by standard treatment with a source of primary amine, for example, Tris or glycine at high pH, ca. 8–10. A substantially pure preparation of protein G can then be obtained by conventional purification procedures.

Figure 1A:
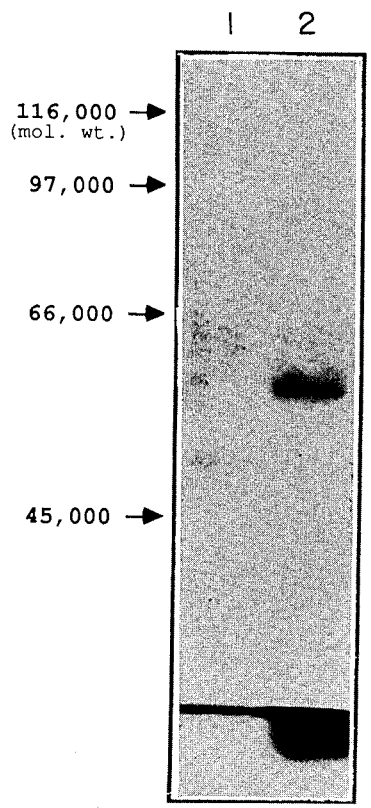
FIG. 1 SDS—PAGE analysis of extracted high molecular weight protein G. IA shows protein A in lane 1 and the CNBr extract in lane 2 stained with Coomassie stain. 1B is the western blot probed with $^{125}$I-human IgG Fc fragments. Lanes 1 and 2 are as in 1A.
Figure 1B:
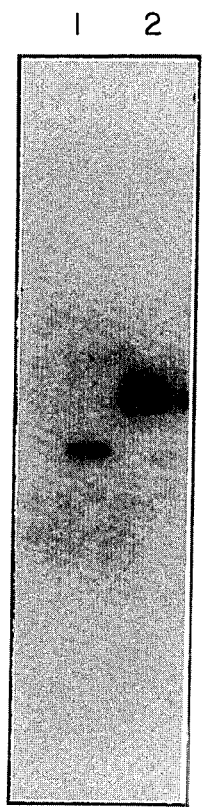

The invention extraction procedure results in the solubilization of a predominantly single form of functionally active protein G with a molecular weight of ca. 52,000 (FIG. 1A). This predominant large molecular weight protein has the ability to bind to the Fc region of IgG (FIG. 1B).

Reagent grade cyanogen bromide can be used in the process at a concentration of about 5 mg to about 25 mg per ml of a suspension of bacterial cells in about 0.1 M HCl. The bacterial cells can be any protein G producing group G or group C streptococci. The detection of the presence of protein G is done by procedures well-known in the art, e.g., assays showing binding to the Fc region of IgG. See Reis, K. J. Ayoub, E. M. and Boyle, Michael D. P. (1983) "Detection of receptors for Fc region of IgG on streptococci," J. Immunol Methods 59:83-94. This article is also referred to, and incorporated herein, for a disclosure of the uses of protein G.

Figure 2:
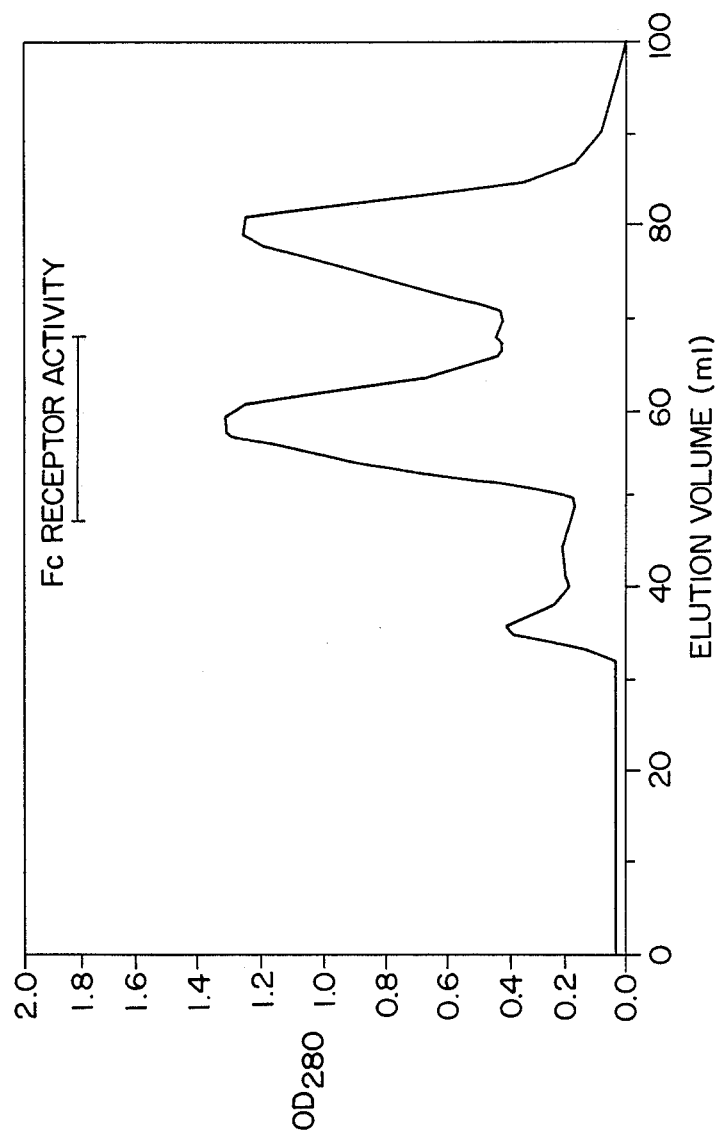
FIG. 2—FPLC column profile of extracted material.
Figures 4A, 4B:
FIG. 4 —Stained SDS-PAGE and western blot pattern of extracted proteins recovered from the active peak of the FPLC column. See FIG. 2. In 4A, 10 μg stainéd with Coomassie stain. 4B is the western blot probed with $^{125}$I-human serum albumin.

Following the extraction of the protein G by cyanogen bromide, the bacterial pellet can be removed by either filtration or centrifugation The extracted material, once isolated by standard molecular sieving chromatography on an FPLC column (FIG. 2) and its chemically reactive carboxy terminus blocked, retains its functional activity and a homogenous protein can be obtained. FIG. 3 demonstrates the stained SDS-PAGE and western blot pattern after transferring the proteins onto nitrocellulose and probing with radiolabeled human Fc fragments. This single molecule also maintains the ability to bind to human serum albumin (FIG. 4) in accordance with previous reports for wild-type protein G. The purified extracted protein has amino acid composition documented in Table 1, and the amino terminal sequence shown in Table 2. The yield of protein G extracted by this procedure is routinely between 0.3 and 0.7 mg per gram wet weight of bacteria. The protein isolated in this way can be radiolabeled without loss of functional activity and can be used as a tracer for a variety of radioimmunoassays. It can also be labeled with biotin, or directly with an enzyme, and used in ELISA. Similar studies have been carried out to demonstrate that the receptor once treated with a fluorescent tag can be used for fluorescent immunoassays. Furthermore, extracted receptor has been combined with colloidal gold and used in EM studies.

The wild type protein G of the invention can be distinguished from the recombinant form of the protein by having the ability to bind not only to the Fc region of human IgG, but also to human albumin. The human albumin binding region is located at the N terminal portion of the molecule and it can bind IgG in the presence of albumin, indicating that the two sites are distinct and function independently. Thus, the albumin reactivity can be of value as a method for orienting the protein G to obtain an immobilized form of the molecule in which the immunoglobulin binding domains are located away from the inert support to maximize IgG binding potential.

Following are examples which illustrate procedures, including the best mode, for practicing the invention. These examples should not be construed as limiting. All percentages are by weight and all solvent mixture proportions are by volume unless otherwise noted.

EXAMPLE 1

Extraction of protein G from a group G or group C streptococcus

A group G or group C streptococcus culture, of which many are known and available to the public, from, for example, the ATCC repository in Rockville, MD, USA, is grown under standard conditions until a sufficient titer of protein G is present. The bacterial cells are then treated with cyanogen bromide (15 mg/ml in 0.1 M HCl) for about 18 hr at room temperature. At the end of this time the bacterial pellet is removed by either filtration or centrifugation. The resulting soluble phase contains large quantities of Fc receptor protein.. This protein can be concentrated and dialyzed (to remove residual cyanogen bromide). A substantially pure preparation of protein G can be obtained by conventional molecular sieving chromatography, followed by treatment with a source of primary amine, for example, Tris or glycine at high pH, ca. 8-10, to block the chemically reactive homoserine carboxy terminal residue.

Protein G, as disclosed previously, can be used for various purposes because, as a bacterial Fc receptor, it can bind to the Fc region of various antibodies with a high affinity. Thus, protein G can be used to detect and isolate various antibodies by procedures known in the art.

TABLE 1

| Amino Acid Composition of Purified CNBr Extracted Material. | | | |
|---|---|---|---|
| Residue | % | Residue | % |
| ASP | 13.5 | ILE | 3.4 |
| THR | 10.7 | LEU | 7.8 |
| SER | 4.3 | TYR | 3.7 |
| GLU | 11.9 | PHE | 1.9 |
| PRO | 2.4 | HIS | 0.4 |
| GLY | 5.7 | LYS | 10.0 |
| ALA | 15.1 | ARG | 1.2 |
| VAL | 7.9 | | |

TABLE 2

| Amino Terminal Sequence of Purified Protein G |
|---|
| Val—Asp—Ser—Pro—Ile—Glu—Asp—Thr—Pro—Ile |

We claim:

1. A process for recovering protein G from wild-type group G or group C streptococci which comprises
   (a) extracting protein G with cyanogen bromide from group G or group C streptococcus bacteria to obtain a soluble phase containing protein G;
   (b) concentrating and dialyzing said soluble phase containing protein G to obtain a concentrate; and
   (c) treating said concentrate with a source of primary amine at a pH of about 8 to about 10 to obtain a concentrated preparation of protein G wherein the chemically reactive homoserine carboxy terminal residue has been blocked.

2. The process, according to claim 1, wherein said cyanogen bromide is at a concentration of about 5 mg to about 25 mg per ml of a suspension of bacterial cells in about 0.1 M HCl.

3. The process, according to claim 2, wherein said cyanogen bromide is at a concentration of about 15 mg/ml of a suspension of bacterial cells in about 0.1 M HCl.

4. The process, according to claim 1, wherein said source of primary amine is Tris or glycine.

5. A process for preparing a substantially pure preparation of protein G from wild-type group G or group C streptococci which comprises
   (a) extracting protein G with cyanogen bromide from group G or group C streptococcus bacteria to obtain a soluble phase containing protein G;
   (b) concentrating and dialyzing said soluble phase containing protein G to obtain a concentrate;
   (c) treating said concentrate with a source of primary amine at a pH of about 8 to about 10 to obtain a concentrated preparation of protein G wherein the chemically reactive homoserine carboxy terminal residue has been blocked; and
   (d) purifying said concentrated preparation of protein G to obtain a substantially pure preparation of protein G.

6. The process, according to claim 5, wherein said cyanogen bromide is at a concentration of about 5 mg to about 25 mg per ml of a suspension of bacterial cells in about 0 I M HCl 7. The process, according to claim 6, wherein said cyanogen bromide is at a concentration of about 15 mg/ml of a suspension of bacterial cells in about 0.1 M HCl.

8. The process, according to claim 5, wherein said source of primary amine is Tris or glycine.

9. The process, according to claim 5, wherein said purification is by conventional molecular sieving chromatography or ion exchange chromatography.

* * * * *

UNITED STATES PATENT AND TRADEMARK OFFICE
CERTIFICATE OF CORRECTION

PATENT NO.    : 4,945,157

DATED         : July 31, 1990

INVENTOR(S)   : Michael D.P. Boyle, Ervin Faulmann

It is certified that error appears in the above-identified patent and that said Letters Patent is hereby corrected as shown below:

Column 1: line 41: "streptococci The type" should read --streptococci. The type--; line 45: "*zooepidemicus*" should read --*zooepidemicus*.--

Column 2: line 28: "bacteria The" should read --bacteria. The--; line 39: "IA" should read --1A--.

Claim 6: line 4: "0 I" should read --0.1--.

Signed and Sealed this

Twenty-fourth Day of September, 1991

*Attest:*

HARRY F. MANBECK, JR.

*Attesting Officer*          *Commissioner of Patents and Trademarks*